United States Patent [19]

Kohn et al.

[11] Patent Number: 5,776,907
[45] Date of Patent: Jul. 7, 1998

[54] MITOMYCIN OLIGONUCLEOTIDE CONJUGATES

[75] Inventors: Harold L. Kohn; Nam Huh, both of Houston; Timothy P. Kogan, Sugar Land; Ajay A. Rege, Houston, all of Tex.

[73] Assignee: Texas Biotechnology Corporation, Houston, Tex.

[21] Appl. No.: 650,289

[22] Filed: May 20, 1996

[51] Int. Cl.$^6$ .................. A61K 48/00; A61K 31/74; C07H 21/00; C07D 487/14
[52] U.S. Cl. .................. 514/44; 435/6; 435/375; 536/24.5; 548/422
[58] Field of Search ................ 435/6, 240.2, 375; 536/23.1, 24.3, 24.31, 24.32, 24.5, 25.1; 514/44; 935/33, 34

[56] References Cited

U.S. PATENT DOCUMENTS 5,593,974  1/1997  Rosenberg et al. .................. 514/44

OTHER PUBLICATIONS

E. Uhlmann et al. Chem. Rev. 90(4)243-84 '90.
C. Stein et al. Science 261: 1004-12 93.
B. Tsang et al. Cancer Gene Therapy 1(1) 65-71 '94.
J. Milligan et al J. Med. Chem. 36 (14) 1923-37 '93.
R. Stull et al. Pharm. Res. 12(4) 465-83 '95.
H. Marvenda et al. FASEB J. 9(6) A1423 Apr. 24, 1995.
Y. Rojanasakul Adv. Drug Del. Rev. 18: 115-131 ('96).

Primary Examiner—Charles C. P. Rories
Attorney, Agent, or Firm—Rockey, Milnamow & Katz, Ltd.

[57] ABSTRACT

The present invention provides conjugates of mitomycin C or derivatives thereof and oligonucleotides. A conjugate of the present invention corresponds to formula I, below:

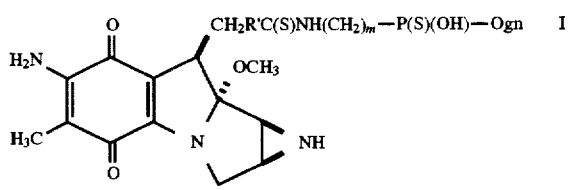

where R is H, $CH_3$, or $C(O)SCH_3$, R' is O or NH, m is an integer from 1 to 10 and Ogn is an oligonucleotide. Pharmaceutical compositions and methods of using such conjugates to inhibit gene product expression are also provided.

16 Claims, 1 Drawing Sheet

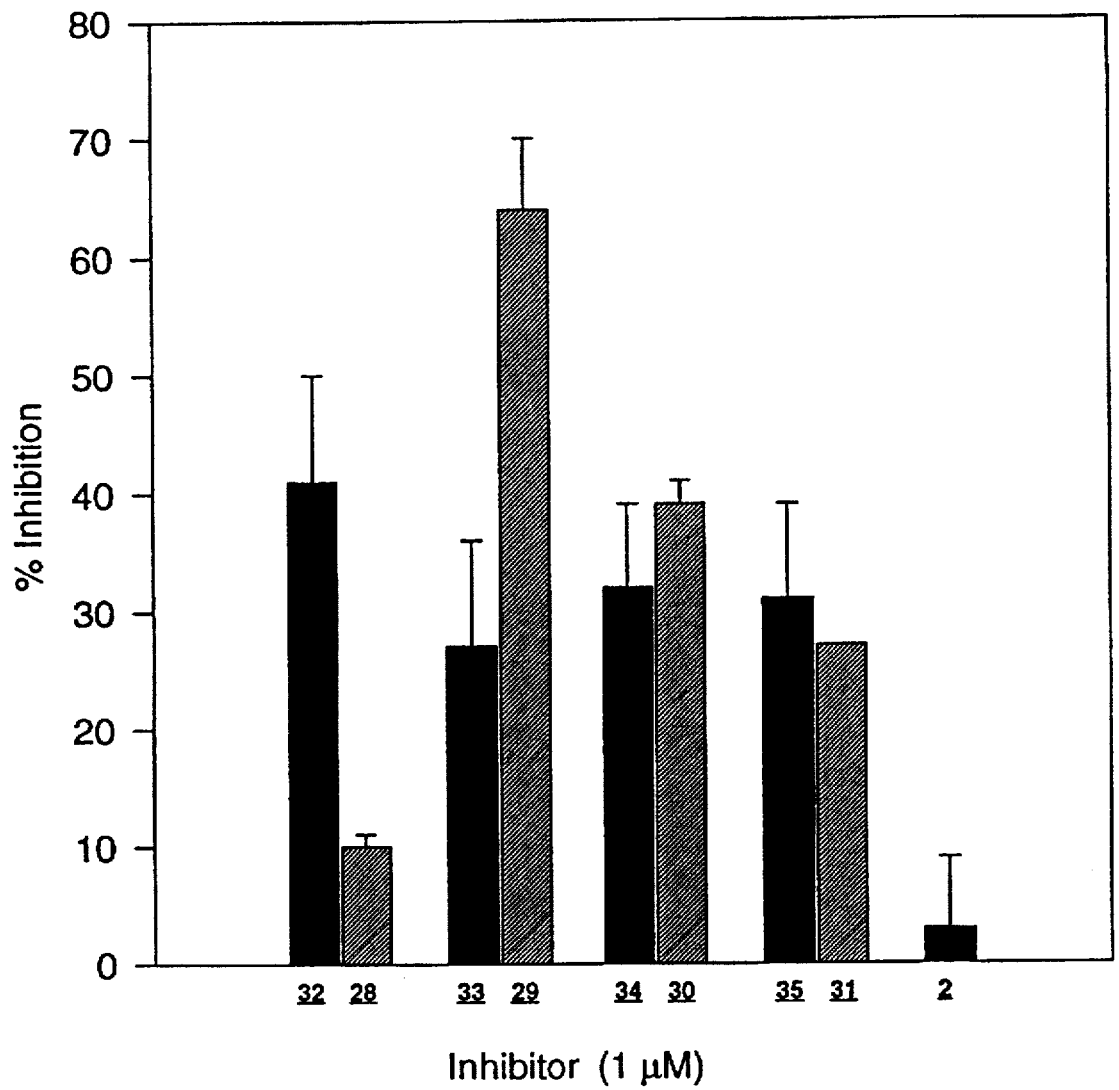

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO:1:

GGCCCCGTGG TGGCTCCAT                                                      1 9

( 2 ) INFORMATION FOR SEQ ID NO:2:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO:2:

AGATGGAAAA GAAATTGCAT GCAGTGCCGG                             3 0

( 2 ) INFORMATION FOR SEQ ID NO:3:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO:3:

GGCACTGCAT GCAATTTCTT TTCCA                            25

( 2 ) INFORMATION FOR SEQ ID NO:4:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO:4:

GCACTGCATG CAATTTCTTT TCCAT                            25

( 2 ) INFORMATION FOR SEQ ID NO:5:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO:5:

CACTGCATGC AATTTCTTTT CCATC                            25

( 2 ) INFORMATION FOR SEQ ID NO:6:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO:6:

ACTGCATGCA ATTCTTTTC CATCT                             25

MITOMYCIN OLIGONUCLEOTIDE CONJUGATES

TECHNICAL FIELD OF THE INVENTION

The field of this invention is antisense agents. More particularly, the present invention pertains to conjugates of mitomycin C and antisense oligonucleotides.

BACKGROUND OF THE INVENTION

Recent years have witnessed technological advances that permit reagents to target specific sequences within single-stranded RNA and DNA (Milligan et al., J. Med. Chem., 1993; Kiely, J. S., Ann. Reports in Med. Chem., 1994; Lown, Anticancer Drug. Des., 1992; Nielsen, Bioconjugate Chem., 1991; Bailly et al., Biochemistry, 1992; McConnaughie and Jenkins, J. Med. Chem., 1995; Wyatt et al., Biochemistry, 1995) and double-helical DNA (Dervan, Science, 1986; Schultz et al., J. Am. Chem. Soc., 1982; Mrksich and Dervan, J. Am. Chem. Soc., 1993; Mrksich and Dervan, J. Am. Chem Soc., 1994; Sluka et al., Science, 1987; Steitz, Q. Rev. Biophys., 1990; Beal and Dervan, J. Am. Chem. Soc., 1992; Koh and Dervan, J. Am. Chem. Soc., 1992; Harrison and Aggarwal, Annu. Rev. Biochem., 1990; Moser and Dervan, Science, 1987; Strobel et al., J. Am. Chem. Soc., 1988; Le Doan et al., Nucleic Acids Res., 1987; Praseuth et al., Proc. Natl. Acad. Sci. U.S.A., 1988; Cooney et al., Science, 1988; Beal and Dervan, Science, 1991; Rajagopal and Feigon, J. Nature, 1989; de los Santos et al., Biochemistry, 1989; Bergstrom and Gerry, J. Am. Chem. Soc., 1994; Povsicet al., J. Am. Chem. Soc., 1992). Drugs known to target and react with DNA include mitomycin C and derivatives thereof (Carter and Crooke, Current Status and New Developments, 1979), which are prototypical bioreductive alkylating agents (Iyer and Szybalski, Science, 1964; Moore and Czerniak, Med. Res. Rev., 1981; Remers, The Chemistry of Antitumor Antibiotics; Wiley: 1979; Franck and Tomasz, In The Chemistry of AntitumorAgents; Wilman: 1990; Fisher and Aristof, Prog. Drug Res., 1988; Tomasz, In Molecular Aspects of Anticancer Drug-DNA Interactions, Macmillan: 1994). The structures of mitomycin C (Compound 1) and its derivatives, porfiromycin (Compound 2), and N(1a)-[(methylthio)carbonyl]mitomycin C (Compound 3), are shown below.

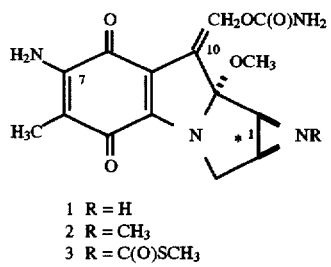

1 R = H
2 R = CH₃
3 R = C(O)SCH₃

Mitomycin C an d it s derivatives, porfiromycin and N(1a)-[(methylthio)carbonyl]mitomycin C, function by quinone reduction permitting alkylation of two DNA bonding sites located at the carbons at positions 1 and 10 of the mitomycin. Alkylation occurs exclusively at guanine (G) residues located within the DNA minor groove (Tomasz et al., Science, 1987). In vitro reductive activation of mitomycin C and porfiromycin leads to preferential alkylaion of 5'-CG* (G*=alkylation site) sites (Li and Kohn, J. Am. Chem. Soc., 1991; Kumar et al., Biochemistry, 1992; Kohn et al., J. Am. Chem. Soc., 1992) while N(1a)-[(methylthio)carbonyl]mitomycin C selectively alkylates 5'AG* and 5'TG* loci (Kohn et al., J. Am. Chem. Soc., 1992). One potential problem, however, with the use of mitomycin C and its derivatives is toxicity resulting from indiscriminate alkylation of DNA guanine (G) residues. There is, therefore, a need in the art for mitomycin C compounds that have the ability to bond and alkylate DNA but have reduced toxicity.

Antisense oligonucleotides (De Mesmaeker et al., Acc. Chem. Res., 1995) have been developed to inhibit the expression of gene products, with emphasis given to their potential utility in anti viral (Agrawal, Trends in Biotechnology, 1992) and anticancer therapy (Mercola and Cohen, Cancer Gene Ther., 1995) and to inhibit restenosis and smooth muscle proliferation (Simons et al., Nature, 1992; Pickering et al., J. Am. Chem. Cardiol., 1992; Spier et al., Circulation, 1992; Simons and Rosenberg, Circ. Res., 1992; Biro et al., Proc. Natl. Acad. Sci. U.S.A., 1993; Shi et al., Circulation, 1993). The proposed mode of action of these agents involves complementary base pairing to a sense strand on mRNA leading to activation of RNase H activity, thereby removing a required RNA strand from the cellular machinery.

BRIEF SUMMARY OF THE INVENTION

The present invention provides mitomycin-oligonucleotide conjugates capable of destroying a target mRNA strand by alkylating a specific guanine site upon reductive activation. These conjugates potentiate the efficacy of antisense oligonucleotides that rely solely on RNase H-mediated destruction of their targets. The tethered oligonucleotide-mitomycin C conjugates show reduced toxicity compared with mitomycin C alone (Carter and Crooke, Current Status and New Developments; Academic Press, 1979) since attachment of the mitomycin to the antisense oligonucleofide diminishes indiscriminate alkylation of DNA guanine residues.

A conjugate of the present invention comprises mitomycin C or a derivative thereof conjugated to an antisense oligonucleotide. The oligonucleotide is linked to the mitomycin C derivative through the carbon atom located at position 10 of the mitomycin molecule. The 5' end of the oligonucleotide is conjugated to the mitomycin derivative. The 5' terminus of the oligonucleotide is derivatized to contain a spacer group. A preferred spacer group is an alkylamino group. A preferred alkylamino spacer contains five or six carbon atoms. The bases of the oligonucleotide component are linked by pseudophosphate bonds that are resistant to cleavage by exonucleases or endonucleases. A preferred such pseudophosphate bond is a phosphorothioate bond.

A conjugate of the present invention is prepared by replacing the carbomoyl moiety at position 10 of mitomycin C or its derivatives with an activated nitrogen-containing or sulphur-containing reactive moiety and then reacting that derivatized mitomycin C with an alkylamino oligonucleotide.

In another aspect, the present invention also provides pharmaceutical compositions containing conjugates of the present invention and methods for using such compositions. Thus, the present invention still further provides a process of inhibiting expression of a gene product in a cell. In accordance with such a process, a cell is contacted with an inhibition-effective amount of a conjugate of the present invention that contains an antisense oligonucleotide complementary to a contiguous portion of a DNA or mRNA molecule in the cell that encodes the desired gene product. Contact with the cell is maintained under biological culture conditions for a period of time sufficient for the conjugate to bond to the encoding DNA or RNA and thus inhibit gene expression. In a particularly preferred embodiment of a process of the present invention, the oligonucleotide component of a conjugate is an antisense oligonucleotide directed against a portion of the human FGFR1 gene and the conjugate is used to inhibit expression of the FGFR1 gene product in vascular smooth muscle cells. Inhibition of FGFR1 gene product expression in vascular smooth muscle cells results in inhibition of vascular smooth muscle proliferation in those cells.

BRIEF DESCRIPTION OF THE DRAWING

In the drawing, which forms a portion of the specification, FIG. 1. shows inhibition of high affinity bFGF binding by Oligonucleotide (Ogn)-Porfiromycin conjugates. Compounds were tested at 1 µM for their ability to inhibit high affinity binding of bFGF to cultured human aortic smooth muscle cells. Results are expressed as percent inhibition when compared to binding in untreated control cells. Un-conjugated compounds are shown as solid bars and the adducts are shown as shaded bars.

DETAILED DESCRIPTION OF THE INVENTION

I. Compositions of Matter.

In one aspect, the present invention provides conjugates of mitomycin C or derivatives thereof and oligonucleotides. A conjugate of the present invention corresponds to formula I, below:

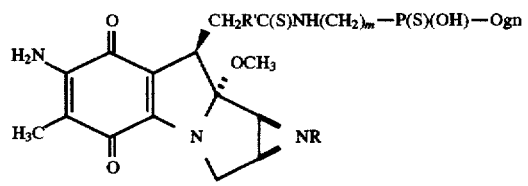

where R is H, CH$_3$, or C(O)SCH$_3$, R' is O or NH, m is an integer from I to 10 and Ogn is an oligonucleotide. In a preferred embodiment, R is C(O)SCH$_3$ or CH$_3$. Even more preferably, R is CH$_3$. Preferably, R' is NH. Preferably, m is from 3 to 8 and, even more preferably, 5 or 6.

The oligonucleotide (Ogn) component of the conjugate contains from about 10 to about 50 individual nucleotides. Preferably, the length of the oligonucleotide is of from about 20 to about 40 nucleotides and, even more preferably, from about 20 to about 30 nucleotides. The oligonucleotide component of the conjugate is an antisense molecule. That is, the sequence of nucleotides within the oligonucleotide is designed to be complementary to a target polynucleotide such as genomic DNA or mRNA. Thus, the particular sequence of an oligonucleotide in a conjugate will vary with the sequence of the target DNA or RNA strand. As set forth hereinafter in the examples, compositions of the present invention have been made wherein the oligonucleotide component is complementary to the translation initiating region of the human A-raf-1 gene and a 30-base-long region in the transcript from the human FGFR1 gene.

The 5' terminus of the oligonucleotide component is derivatized to contain a sapcer group (e.g., an alkylamino spacer [NH(CH$_2$)$_m$]). The alkylamino spacer contains 1 and 10 carbon atoms. Preferably, the spacer contains from 3 to 8 carbon atoms and, even more preferably, 5 or 6 carbon atoms. Thus, in the most preferred embodiment, the alkylamino is pentylamino or hexylamino. In a preferred embodiment, the bases of the oligonucleotide are linked by pseudophosphate bonds that are resistant to cleavage by exonuclease or endonuclease enzymes. Exonuclease enzymes hydrolyze the terminal phosphodiester bond of a nucleic acid. Endonuclease enzymes hydrolyze internal phosphodiester bonds of a nucleic acid.

By replacing a phosphodiester bond with one that is resistant to the action of exonucleases or endonucleases, the stability of the nucleic acid in the presence of those exonucleases or endonucleases is increased. As used herein, pseudophosphate bonds include, but are not limited to, methylphosphonate, phosphomorpholidate, phosphorothioate, phosphorodithioate and phosphoroselenoate bonds. Additionally, exonuclease and/or endonuclease resistant oligonucleotides can be obtained by blocking the 3' and/or 5' terminal nucleotides with substituent groups such as acridine.

Preferred pseudophosphate bonds are phosphorothioate bonds. The pseudophosphate bonds may comprise the bonds at the 3' and or 5' terminus, the bonds from about one to about five of the 3' and/or 5' terminus bases, or the bonds of the entire oligonucleotide. A preferred oligonucleotide with pseudophosphate bonds is one in which all of the bonds are comprised of pseudophosphate bonds.

DNA or RNA oligonucleotides can be prepared using several different methods, as is well known in the art [See, e.g., Ausubel et al., (eds.), Current Protocols in Molecular Biology, John Wiley & Sons, New York (1990)]. The phosphoramidite synthesis method is described in Caruthers et al., Meth. Enzymol., 154:287 (1987); the phosphorothioate oligonucleotide synthesis method is described in Iyer et al., J. Am. Chem. Soc., 112:1253 (1990). The oligonucleotide component, including the alkylamino spacer, is ligated or tethered to mitomycin C, or a derivative thereof, at the carbon atom located at position 10 of mitomycin C.

Conjugates of the present invention are prepared by replacing the carbomoyl moiety at position 10 of mitomycin C with an activated nitrogen-containing or sulphur containing reactive moiety and then reacting the mitomycin C derivative with the alkylamino oligonucleotide.

Although strategies to modify the C(7) loci exist (Iyengar et al., J. Med. Chem., 1983; Iyengar et al., J. Med. Chem., 1983; Kono et al., J. Antibiot., 1993; Sawhney and Kohn, J. Med. Chem., 1989) and N(1 a) (Fishbein and Kohn, J. Med. Chem., 1987; De Marre et al., J. Control. Release, 1995; De Marre et al., J. Control Release, 1994), few methods exist for the modification of the C(10) site (Kasai and Kono, Syn. Lett., 1992; Choi et al., J. Org. Chem., 1995). Attachment of an antisense oligonucleotide to the C(10) site, however, permits subsequent DNA bonding at C(1) with minimal distortion of the DNA duplex. Several criteria were established for the synthesis of C(10) mitomycin-oligonucleotide conjugates. First, the coupling of the mitomycin with the oligonucleotide had to proceed efficiently in aqueous solutions. Second, the mitomycin-oligonucleotide conjugates had to be sufficiently stable in vitro and in vivo so as to permit assessment as antisense reagents. Third, the mitomycin-oligonucleotide conjugates had to be separable from the starting oligonucleotides to permit their purification and characterization. Exemplary structures of C(10) modified mitomycin compounds that, when conjugated to oligonucleotides, satisfy these criteria are set forth below.

The porfiromycin substrates, Compounds 5, 6, and 9, shown below, were designed to target mRNA sequences that contained 5'CG* sites at the 5' termini (Li and Kohn, *J. Am. Chem. Soc.*, 1991; Kumar et al., *Biochemistry*, 1992; Kohn et al., *J. Am. Chem. Soc.*, 1992) whereas Compounds 7 and 8, also shown below, were

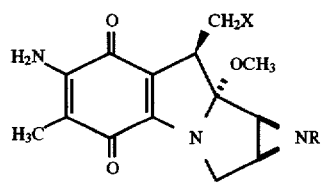

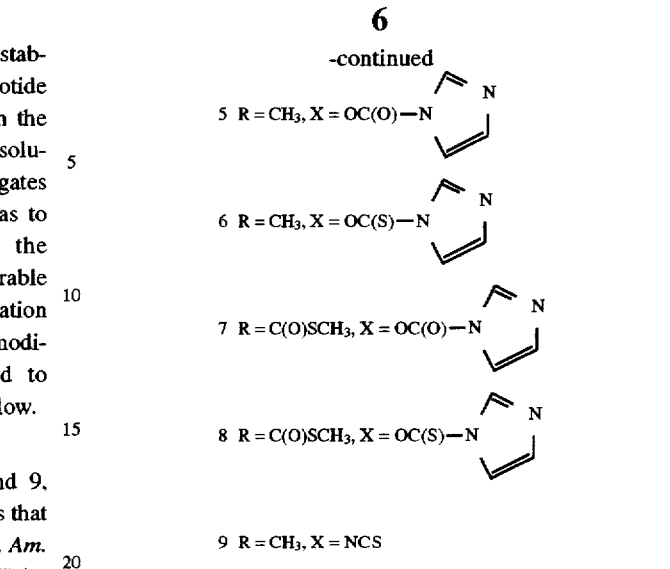

designed to react preferentially with mRNAs having an appropriately disposed 5'AG* or 5'TG* site (Kohn et al., *J. Am. Chem. Soc.*, 1992).

In general, two different synthetic strategies can be used to prepare the C(10) derivatives of mitomycin C. Separate strategies were developed for the synthesis of Compounds 5–8 and for Compound 9. In the first strategy (See Scheme 1, below), decarbamoylation of mitomycin C (Compound 1) with sodium methoxide in benzene afforded 10-decarbamoylmitomycin C (Choi et al., *J. Org. Chem.*, 1995; Milligan et al., *J. Med. Chem*, 1993; Varma, *Syn. Lett.*, 1993; Kinoshita et al., *J. Med. Chem.*, 1971) (Compound 10).

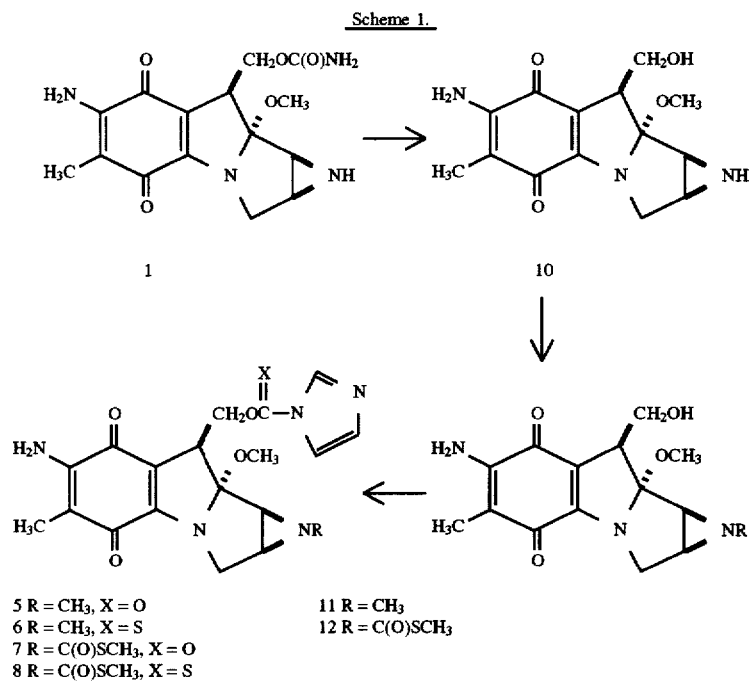

Functionalization of the N-aziridine group with dimethylsulfate or methylthiochloroformate and base yielded the N-substituted mitomycins Compounds 11 and 12, respectively. The N-aziridine substituted 10-decarbamoylmitomycins were then reacted with 1,1'-carbonyldiimidazole or 1,1'-thiocarbonyldiimidazole to yield Compounds 5-8.

The second strategy used replacement of the C(10) hydroxy group in 10-decarbamoylporfiromycin (Choi et al., J. Org. Chem., 1995; Milligan et al., J. Med. Chem., 1993; Varma, Syn. Lett., 1993; Kinoshita et al., J. Med. Chem., 1971) (Compound 11) with an amino unit (See Scheme 2 below).

Compounds 5-9 were fully characterized, and their spectroscopic properties were consistent with the proposed structures. As anticipated, placement of a carbonyl or a thiocarbonylimidazole unit at C(10) led to a downfield shift in the $^1$H NMR for the C(10) methylene protons compared with the starting alcohols Compounds 11 and 12 (Kohn et al., J. Am. Chem. Soc., 1987).

Once formed, the C(10) modified mitomycin C derivatives are dissolved in an aqueous buffer and reacted with an alkylamino oligonucleotide to form the final conjugate. As is well known in the art, selection of appropriate aqueous buffer and reaction conditions will depend on the exact nature of the C( 10) modification to the mitomycin C

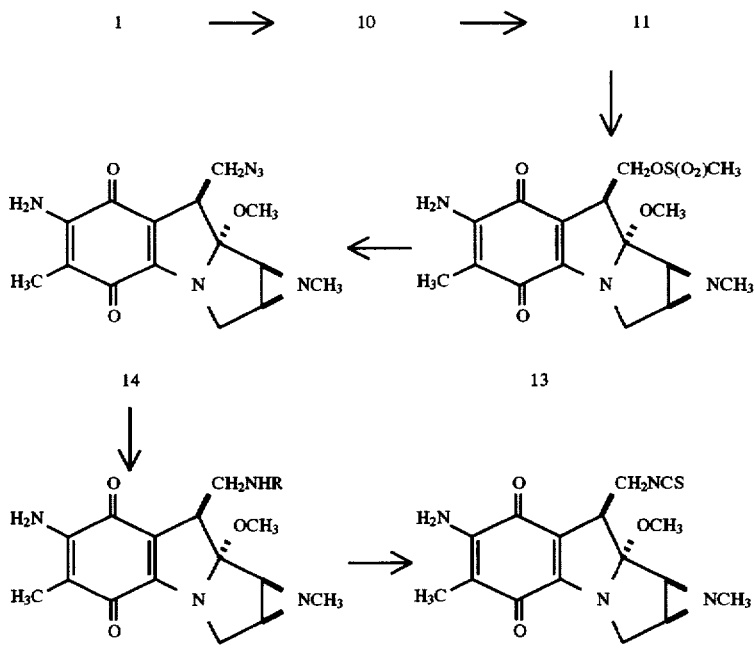

15 R = H
16 R = C(O)CH$_3$

This interchange was accomplished in three steps with a 21% overall yield. First, the C(10) site in Compound 11 was activated by conversion to the C(10) mesylate Compound 13 (Kasai and Kono. Syn. Lett. 1992; Choi et al., J. Org. Chem., 1995; Urakawa et al., J. Antibiot., 1981; Kono et al., J. Antibiot., 1990) and then treated with NaN$_3$ in dimethylformamide at 90° C. to give C(10) azide Compound 14 in a 68% isolated yield. Reduction of the C(10) azide group in Compound 14 to the amino Compound 15 in the final step without concomitant reductive activation and destruction of the mitosane ring system was accomplished by catalytic reduction (PtO$_2$, H$_2$) in pyridine followed by air oxidation. This method took advantage of Danishefsky and coworkers' discovery that mitomycin quinone reduction in pyridine proceeds without loss of methanol at C(9) and C(9a) (Danishefsky and Ciufolini, J. Am. Chem. Soc., 1984). Amine Compound 15 was characterized as the free base and by conversion to the N-acetyl derivative Compound 16. Conversion of Compound 15 to N(1a)-methyl- 10-des (carbamoyloxy)-10-isothiocyanatomitomycin C (Compound 9) occurred smoothly with di-2-pyridyl thionocarbonate (DPT).

derivative. By way of example, where the C(10) modification results in there being a carbonyl- or thiocarbonylimidazole unit at that position (Compounds 5-8), an appropriate buffer can be a 20% methanolic-aqueous borax solution having a pH of 8.0 or an aqueous solution with 4-dimethylaminopyridine. By way of further example, where the modification at C(10) is an isothiocyanate (Compound 9), conjugation to an oligonucleotide can take place in an aqueous buffered solution of dimethyl formamide in sodium bicarbonate at a pH of about 9.0.

Means for determining appropriate buffers and reaction conditions are readily ascertainable by one of ordinary skill in the art. The conjugation of a C(10) activated mitomycin C to an alkylamino oligonucleotide can be tested with a methyl ester of an amino acid instead of a complete oligonucleotide. One such methyl ester amino acid for use in determining reaction conditions is glycine methyl ester hydrochloride (Compound 17). By way of example, glycine methyl ester hydrochloride (3.3-5.5 equiv.) was added to methylene chloride solutions containing Compounds 5-8 and 4-dimethylaminopyridine to yield the C(10)-coupled carbamates Compounds 18 and 20 and the thiocarbamates Compounds 19 and 21, the structures of which are given below.

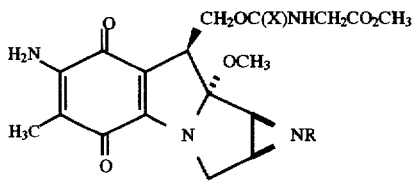

18 R = CH₃, X = O
19 R = CH₃, X = S
20 R = C(O)SCH₃, X = O
21 R = C(O)SCH₃, X = S

The treatment of an aqueous solution (pH 9.0) of Compound 5 with glycine methyl ester hydrochloride (5 equiv.) gave 10-decarbamoylporfiromycin (Compound 11) as the major product rather than Compound 18 (HPLC analysis). Correspondingly, the addition of glycine methyl ester hydrochloride (5 equiv.) to Compound 7 in a 20% methanolic-aqueous borax solution (pH 8.0) furnished the desired adduct Compound 20 in a 36% isolated yield. Improved coupling yields were observed for the two 10-decarbamoyl-10-thiocarbonylimidazoles Compounds 6 and 8. Both Compounds 6 and 8 reacted with glycine methyl ester hydrochloride (5–6 equiv.) in 20% methanolic-aqueous borax solutions (pH 8.0) to give Compounds 19 and 21, respectively, in high yields (>95%, HPLC analysis).

Based on the efficiency of coupling reactions with Compounds 6 and 8, Compound 8 was reacted with the hexylamino tethered DNA, $H_2N(CH_2)_6$-P(S)(OH)-GGCCCCGTGGTGGCTCCAT (SEQ ID NO:1). This 19 mer oligonucleotide complements a 19-base sequence in the translation initiation region of the human A-raf-1 gene (Beck et al., Nucleic Acids Res., 1987). This gene product has been linked to smooth muscle cell proliferation following angioplasty. Preliminary optimization reactions indicated that use of excess amounts of Compound 8 (28 equiv.) in 10% acetonitrile-0.08M Tris-HCl aqueous buffered solutions maintained at pH 8.3 gave a 36% yield of a new DNA product (Compound 23, below) along with the major mitosane byproducts Compounds 10 and 12.

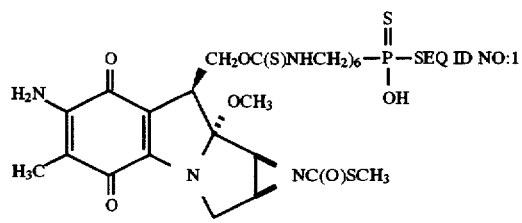

23

Repetition of this reaction on a semi-preparative scale and separation of the product mixture by preparative HPLC satisfactorily removed the coupled mitomycin-DNA adduct from the mitomycin byproducts (i.e., Compounds 10, 12) but did not completely separate the product from the starting oligonucleotide (UV-visible analysis). The observed low yield of Compound 23 was attributed to the competitive hydrolytic cleavage of the oxy(thiocarbonyl)imidiazole moiety in Compound 8 rather than to the instability of the product Compound 23 under the study conditions. This assumption was based, in part, upon the identification of Compounds 10 and 12 as major byproducts in the reaction and upon the observation that N-methyl ethylthiocarbamate did not undergo hydrolysis in $D_2O$ solutions maintained at 22° C. for 4 days.

Isothiocyanates, such as in Compound 9, can be coupled to amines in aqueous solutions (Avalos et al., Tetrahedron, 1994). Accordingly, reaction of Compound 9 with glycine methyl ester hydrochloride in aqueous Tris-HCl solutions gave Compound 25, below, in a 61% yield (HPLC analysis). The DNA coupling conditions were defined by HPLC monitoring of a series of analytical reactions of Compound 9 with SEQ ID NO:1 where the DNA concentration, ratio of Compound 9 to SEQ ID NO:1, buffer composition (concentration, pH, organic co-solvent), and reaction temperature were systematically varied. High concentrations of DNA with 5–6 equivalents of Compound 9 in a 50% dimethylformamide-aqueous 0.1M $NaHCO_3$ (pH 9.0) buffer system resulted in the formation of Compound 26, below.

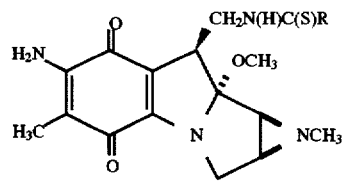

25 R = NHCH₂CO₂CH₃
26 R = NH(CH₂)₆—P(S)(OH)—SEQ ID NO:1

Based on the data set forth above, a series of porfiromycin-oligonucleotide conjugates were prepared on a semi-preparative scale. A 30-base-long region in the transcript from the human FGFRI gene (n566 to n595; Genbank sequence accession number X52833) (Doinne et al., Embo J., 1990) was chosen as a target. The sequence of that target is 5'-AGATGGAAAA GAAATTGCATG CAGTGCCG*G-3'(SEQ ID NO:2), where the asterisk indicates the target G nucleotide. This base sequence has low C content and has a CG*G sequence at the 3' end. Porfiromycin preferentially alkylates this trinucleotide sequence upon in vitro reductive activation (Kohn et al., J. Am. Chem. Soc., 1992). To determine the geometric requirements needed by the hexylamino spacer unit in the antisense oligonucleotides for mRNA alkylation (Chatterijee and Rokita, J. Am. Chem. Soc., 1994; Li et al., Bioconjugate Chem, 1994), a series of 25-mer DNA conjugates in which the antisense oligonucleotide was systematically displaced from the targeted CG*G site on the sense mRNA strand were prepared (See Compounds 28–31, below).

| Antisense Strands | Compound No |
|---|---|
| SEQ ID NO: 3-P(S)(OH)—(CH₂)₆NH—M | 28 |
| SEQ ID NO: 4-P(S)(OH)—(CH₂)₆NH—M | 29 |
| SEQ ID NO: 5-P(S)(OH)—(CH₂)₆NH—M | 30 |
| SEQ ID NO: 6-P(S)(OH)—(CH₂)₆NH—M | 31 | where M =

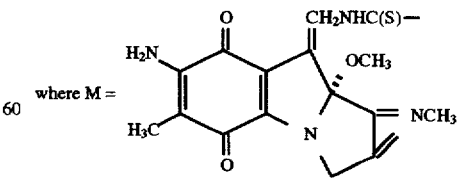

Oligonucleotides (Compounds 32–35, see below) were treated with 5-6 equivalents of Compound 9 for 23–30 hours at room temperature.

| | Compound No |
|---|---|
| SEQ ID NO:3P(S)(OH)—(CH$_2$)$_6$NH$_2$ | 32 |
| SEQ ID NO:4P(S)(OH)—(CH$_2$)$_6$NH$_2$ | 33 |
| SEQ ID NO:5P(S)(OH)—(CH$_2$)$_6$NH$_2$ | 34 |
| SEQ ID NO:6P(S)(OH)—(CH$_2$)$_6$NH$_2$ | 35 |

In Compound 28, the attached porfiromycin is one residue from the projected guanine (G*) bonding site, in Compound 29 it is two residues away, in Compound 30 it is three residues away, and in Compound 31 it is four residues away. The oligonucleotide stock solutions prepared for the coupling reaction with Compound 9 ranged from 52.3, µM for Compound 35 to 395.4 µM for Compound 32.

HPLC analysis prior to work-up indicated near complete utilization of the starting oligonucleotide with the highest percentage of oligonucleotide consumption observed for the most concentrated oligonucleotide solutions. Semipreparative HPLC purification of the reaction mixtures provided the conjugates Compounds 28–31 in a 12% to near quantitative isolated yield. Three experimental criteria established the identities of Compounds 28–31. First, a new peak in the HPLC profile near the starting oligonucleotide (Compounds 32–35) that absorbed at 365 nm in the ultraviolet-visible spectrum (Webb et al., *J. Am. Chem. Soc.*, 1962) was observed. This absorption value is characteristic for porfiromycin. Second, the relative ultraviolet-visible absorption values at 360 versus 260 nm for the purified adducts were in excellent agreement with the predicted values (Borowy-Borowski et al., *Biochemistry*, 1990). Third, conjugates Compounds 28–31 all exhibited a parent ion in the electrospray mass spectrum consistent with their proposed structures. Moreover, each conjugate (Compound 28–31) displayed an ion 34±2 mass units higher than the starting unmodified oligonucleotide (Compounds 32–35). This differential mass corresponded to the molecular weight of Compound 9.

II. Pharmaceutical Compositions

In another aspect, the present invention provides a pharmaceutical composition comprising a conjugate of the present invention and a physiologically tolerable diluent.

The present invention includes one or more conjugates of the present invention as described above formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally (intravenous, by intramuscularly or subcutaneously), intracisternally, intravaginally, intraperitoneally, locally (powders, ointments or drops), or as a buccal or nasal spray.

The compositions can also be delivered through a catheter for local delivery at the site of vascular damage, via an intracoronary stent (a tubular device composed of a fine wire mesh), or via a biodegradable polymer. The compositions may also be complexed to ligands, such as antibodies, for targeted delivery of the compositions to the site of smooth muscle cell proliferation.

The compositions are, preferably, administered via parenteral delivery at the local site of smooth muscle cell proliferation. The parenteral delivery is, preferably, via catheter.

Compositions suitable for parenteral injection may comprise physiologically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a conjugate of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

The agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are phospholipids and phosphatidyl cholines (lecithins), both natural and synthetic.

Methods of forming liposomes are known in the art. See, for example, Prescott, Ed., *Methods in Cell Biology*, Volume XIV, Academic Press, New York, N.Y. (1976), p. 33 et seq.

III. Process of Inhibiting Expression of a Gene Product

The present invention is further directed to a process of inhibiting expression of a gene product in a cell. The process includes the steps of contacting the cell with an inhibition-effective amount of a conjugate of the present invention that contains an antisense oligonucleotide the sequence of which is complementary to a contiguous portion of a DNA or mRNA molecule that encodes the gene product, with the conjugate bonding to the encoding DNA and RNA. Contact is maintained under biological culture conditions for a period sufficient for inhibition of expression.

As used herein, an "inhibition-effective amount" is that amount of a conjugate of the present invention which is sufficient for inhibiting the expression of a desired gene product in a cell contacted with such a conjugate. Means for determining an inhibition-effective amount in a particular subject will depend, as is well known in the art, on the nature of the conjugate used, and the mass of the subject being treated. A process of inhibiting gene product expression can be used with any cell. The process has particular utility for proliferating cells such as cancer cells.

Biological culture conditions are those conditions necessary to maintain growth of the cells in a normal, conjugate-free environment. These biological culture conditions, encompassing such factors as temperature, humidity, atmosphere, pH and the like. A preferred conjugate useful in this process has the structure of formula I, above.

The present invention is still further directed to a process for treating vascular smooth muscle cell proliferation that comprises administering to a host mammal in need of such treatment an effective amount of a conjugate having the structure of any of Compounds 28–31.

A host mammal in need of the treatment of a process for the inhibition of vascular smooth muscle cell proliferation suffers from a disease state in which such proliferation is implicated or is undersgoing a therapeutic procedure that may induce proliferation. Exemplary disease states and procedures include vascular stenosis, post-angioplasty restenosis (including coronary, carotid and peripheral stenosis), other non-angioplasty reopening procedures such as atherectomy and laser procedures, atherosclerosis, atrial-venous regulation of FGFR1. FIG. 1 shows that un-conjugated porfiromycin did not inhibit high affinity binding sites, whereas un-conjugated Ogns caused partial inhibition of high affinity binding sites. Compound 29 showed inhibition of high affinity binding that was significantly higher than that caused by the corresponding un-conjugated Ogns Compound 33.

Human aortic smooth muscle cells were plated in 96 well plates (3,000 cells/well) and grown for 24 hr in DMEM (Dulbecco's Minimal Essential Medium) containing 10% fetal bovine serum (FBS). The following day, wells were treated with inhibitors. Cell proliferation was quantitated 4 days later by counting cells in a Coulter Counter.

In contrast to the results from bFGF binding experiments, the cell proliferation assay (See Table 1, below) showed that un-conjugated porfiromycin (Compound 2) significantly inhibited HASMC growth at 1 mM, and was toxic at higher concentrations as evidenced by >100% inhibition. Both the un-conjugated Ogns and the Ogn- porfiromycin conjugates caused significant inhibition of HASMC growth, but were less potent than porfiromycin alone. Compound 29 was the most potent among the 4 conjugates and was more potent than its un-conjugated Ogn Compound 33. Moreover, in contrast to porfiromycin, the Ogn-porfiromycin conjugates showed no cellular toxicity even at the highest concentration used.

TABLE 1

Inhibition of Proliferation of Cultured Human Aortic Smooth Muscle Cells by Ogn-Porfiromycin Conjugates

| Conc (mM) | Compound 32 | Compound 28 | Compound 33 | Compound 29 | Compound 34 | Compound 30 | Compound 35 | Compound 31 | Compound 2 |
|---|---|---|---|---|---|---|---|---|---|
| 1 | 27 (4)* | 43 (7) | 43 (11) | 45 (3) | 40 (4) | 45 (3) | 47 (4) | 37 (4) | 89 (4) |
| 3 | 30 (10) | 61 (1) | 46 (2) | 72 (2) | 60 (5) | 58 (6) | 60 (2) | 40 (12) | 104 (1) |
| 10 | 64 (9) | 86 (1) | 60 (6) | 100 (2) | 62 (8) | 83 (2) | 73 (1) | 78 (1) | 126 (2) |

*Numbers shown are percent inhibition (SEM) when compared to untreated control.

shunt failure, cardiac hypertrophy, vascular surgery, coronary artery bypass graft and organ transplant. In a preferred embodiment, the conjugate as described above is dissolved or dispersed in a physiologically tolerable diluent.

Human aortic smooth muscle cells (HASMC) in culture were incubated at 37° C. with 1 µM of un-conjugated antisense Ogns (Compounds 32–35), porfiromycin (Compound 2), or Ogn-porfiromycin (Compounds 28–31) conjugates. $^{125}$I-bFGF was purchased from Biomedical Technologies Inc., Mass. Human aortic smooth muscle cells (P3 to P9; 9,000 cells/well) were grown to 80–90% confluency in a 48-well culture dish. The growth medium was removed and cells were incubated at 37° C. for 24 hours with 1 µM inhibitor in binding buffer (25 µM Hepes, pH 7.4, 1 µg/µL BSA; 200 µL/well). Cells were washed with 300 µL PBS, and then incubated for 90 min. at room temperature with $^{125}$I-bFGF in binding buffer. Nonspecific binding was determined by adding to a few wells 300 ng unlabelled human recombinant bFGF. Wells were then washed sequentially with 300 µL PBS, 300 µL of heparin ( 250 µg/µL in PBS ), and again with 300 ml PBS. The cells were lysed by incubation for 15 min. at room temperature with 300 ml 1% Triton X-100 in water. The lysates were collected and high affinity binding was determined by counting the radioactivity in a Beckman LS 6000TA scintillation counter.

A decrease in binding, expressed as a percentage of binding to untreated cells, suggested possible down- These data suggest a preferred length between the end of the antisense recognition unit and the targeted sense guanine residue, a distance spanned by the spacer. The most active conjugate (Compound 29) targets the guanine two residues beyond the end of the antisense sequence, possibly positioning it close to the reactive porfiromycin moiety. Taken together, the biological assay data suggest that the Ogn conjugates are more target-selective and less toxic than either mitomycin or porfiromycin.

The following examples illustrate preferred embodiments of the present invention and are not limiting of the claims and specification.

EXAMPLE 1

Instrumentation, Materials, and Solvents.

Proton ($^1$H NMR) and carbon-13 ($^{13}$C NMR) nuclear magnetic resonance spectra were recorded on either a Nicolet NT-300 or a General Electric QE-300 spectrometer. Chemical shifts are expressed in parts per million relative to the solvent employed, and coupling constants (J values) are given in hertz. Proton—proton interactions were confirmed in selective cases by the COSY spectrum. Mass spectral (MS) data for the non-oligonucleotide adducts were obtained on a Finnigan TSQ-70 triple quadruple mass spectrometer under positive CI conditions by Dr. Mehdi Moini at the University of Texas at Austin. Mass spectrometric analyses of the oligodeoxynucleotides and porfiromycin oligodeoxynucleotide conjugates were conducted at UMIST (Manchester, U.K.) by Ms. Isabel Riba and Dr. Simon J. Gaskell using electrospray (ESI) mass spectrometry on a Quattro tandem quadrupole mass spectrometer (upgraded to Quattro II specifications) supplied by VG Organic, Ltd. (Manchester, U.K.). Samples were prepared using the procedure of McCloskey (Limbach et al., *J. Am. Soc. Mass Spectrom.*, 1995). Samples were introduced to the electrospray interface in isopropanol/water (2/1) and detection was in the negative ion mode. Each analyte gave a series of ions differing in the extent of deprotonation. The masses reported are those after transformation of the m/z data and correspond to the masses of the neutral oligonucleotides. Melting points were determined with a Fisher-Johns melting point apparatus and are uncorrected. Ultraviolet-visible absorption spectra (UV-vis) were run on a Hitachi Model 100-80 spectrometer. FT-IR spectra were run on Mattson Galaxy Series FT-IR 5000 and Genesis infrared spectrophotometers, and absorption values are expressed in wavenumbers (cm$^{-1}$). pH measurements were determined with either a Radiometer pHM 26 or a pHM 84 research meter equipped with a Radiometer GK 2320C combination glass electrode, which was standardized against aqueous buffer solutions.

Analytical HPLC analyses were conducted with the following Waters Associates Units: 510 A pump, 510 B pump, Model 680 gradient controller, Model 490 multiwavelength detector, U6K injector. The peak areas in the HPLC were determined with Waters Associates 740 and 745 and Hewlett Packard 3392A integrators. The products were eluted from a C18 mBondapak (stainless steel) column (3.9×300 mm) using either one of the two following linear gradient conditions. (a) Program 1: 90% A (0.1M triethylammonium acetate, pH 7.0) and 10% B (acetonitrile) isocratic for 5 min., then from 90% A and 10% B to 45% A and 55% B in 30 min. (b) Program 2: 100% A (3 µM triethylammonium phosphate, pH 4.7) and 0% B (3 µM triethylamine in acetonitrile) to 50% A and 50% B in 25 min. In both cases, the column was fitted with a mBondapak guardpak precolumn and a flow rate of 1 µL/min. was used. The eluent was monitored at 260, 313, and 365 nm. The HPLC solvents were filtered (aqueous solution with Millipore HA, 0.45 mm; acetonitrile with Millipore FH, 0.5 mm) and degassed before utilization. For the purification of mitomycin-conjugated oligonucleotides a Rainin HPLC system (flow rate 2.0 µL/min.) connected to a C8 reversed-phase semi-preparative column (5 mM, 25 cm, 10 mm ID) was used employing program 1 where the aqueous triethylammonium acetate solution was maintained at 0.025M.

All water used for the reactions was HPLC grade. Tetrahydrofuran and benzene were both distilled from Na metal and benzophenone, methylene chloride was distilled from P$_2$O$_5$, and ethylene glycol dimethyl ether was distilled from LiAlH$_4$. All other solvents were the best commercial grade available and used without further purification. Thin and thick-layer chromatography were run on pre-coated silica gel GHLF microscope slides (2.5×10 cm; Analtech No. 21521), and silica gel GF preparative uniplates (20×20 cm; Analtech No. 02013).

EXAMPLE 2

Preparation of N(1a)-[(Methylthio)Carbonyl]-10-Decarbamoyl-Mitomycin C (Compound 12).

To an anhydrous ethylene glycol dimethyl ether solution (3 µL) containing Compound 10 (Choi et al., *J. Org. Chem.*, 1995; Kinoshita et al., *Med. Chem.*, 1971) (9.0 mg, 0.03 mmol) and triethylamine (5.2 µL, 0.04 mmol) was added methyl chlorothiolformate (4.1 mg, 3.2 µL, 0.04 mmol) under Ar. The reaction mixture was stirred at room temperature (1 h), and the solvent was removed under reduced pressure. The reaction mixture was purified by TLC (10% methanol-chloroform) to afford Compound 12 (10.0 mg, 89%) as a purple solid: mp 82°–83° C.; HPLC t$_R$ (program 2) 24.1 min., (program 1) 24.5 min.; R$_f$ 0.76 (10% CH$_3$OH—CHCl$_3$); UV-vis (CH$_3$OH) 1$_{max}$ 360 nm; $^1$H NMR (CDCl$_3$) d 1.78 (s, C(6)CH$_3$), 2.32 (s, N(1a)C(O)SCH$_3$), 3.21 (s, C(9a)OCH$_3$), 3.36 (dd, J=1.8, 4.7 Hz, C(2)H), 3.49 (m, C(9)H, overlapped), 3.51 (m, C(3)H$_a$, overlapped), 3.54–3.56 (m, C(1)H, overlapped), 3.93–3.96 (m, C(10)H H'), 4.12 (dd, J=8.4, 10.7 Hz, C(10)HH'), 4.46 (d, J=13.1 Hz, C(3)H$_b$), 5.24 (br, C(7)NH$_2$); $^{13}$C NMR (CDCl$_3$) 7.9, 12.9, 42.1, 43.8, 45.5, 48.8, 49.7, 61.8, 105.0, 105.4, 113.8, 147.2, 154.4, 176.8, 178.3, 180.3 ppm; MS (+CI) m/e (rel intensity) 366 [M+1, 100]$^+$, 348 (223), 304 (9), 154 (55); M$_r$ (+CI) 366.112 25 [M+1]$^+$ (calculated for C$_{16}$H$_{20}$N$_3$O$_5$S, 366.112 36).

EXAMPLE 3

Preparation of N-[10-Decarbamoyl-10-O-Carbonylporfiromycin]-Imidazole (Compound 5).

To a stirred methylene chloride solution (1 µL) of Compound 11 (Choi et al., *J. Org. Chem.*, 1995; Han et al., *J. Org. Chem.*, 1992) (6.8 mg, 0.02 mmol) and 4-dimethylaminopyridine (1.3 mg, 0.01 mmol) was added 1,1'-carbonyldiimidazole (33 mg, 0.20 mmol). The reaction mixture was stirred at room temperature (19 h), and then the solvent was removed under reduced pressure to give a crude purple solid. Purification by TLC (10% methanol-chloroform) afforded Compound 5 (4.0 mg, 45%) as a purple solid: mp 94°–95° C.; HPLC t$_R$ (program 2) 30.3 min.; R$_f$ 0.47 (10% CH$_3$OH—CHCl$_3$); UV-vis (CH$_3$OH) 1$_{max}$ 360 nm; $^1$H NMR (CDCl$_3$) d 1.77 (s, C(6)CH$_3$), 2.19 (m, C(1)H, overlapped), 2.24 (s, N(1a)CH$_3$), 2.29–2.31 (m, C(2)H), 3.20 (s, C(9a)OCH$_3$), 3.49 (dd, J=2.0, 13.0 Hz, C(3)H$_a$), 3.72 (dd, J=5.0, 10.4 Hz, C(9)H), 4.23 (d, J=13.0 Hz, C(3)H$_b$), 4.69 (t, J=10.4 Hz, C(10)H H'), 5.04 (dd, J=5.0, 10.4 Hz, C(10)HH'), 5.20 (br, C(7)NH$_2$), 7.10 (s, imidazole C(4)H), 7.50 (s, imidazole C(5)H), 8.22 (s, imidazole C(2) H); $^{13}$C NMR (CDCl$_3$) 7.9, 42.7, 42.9, 43.2, 45.8, 49.7, 49.8, 65.5, 105.2, 105.7, 109.5, 117.2, 130.8, 137.2, 147.3, 148.3, 154.8, 175.6, 178.4 ppm; MS (+CI) m/e (rel intensity) 218 (52), 186 (12), 129 (100), 115 (30), 111 (42), 106 (12); M$_r$ (+CI) 400.160 79 [M+1]$^+$ (calculated for C$_{19}$H$_{22}$N$_5$O$_5$, 400.162 09).

EXAMPLE 4

Preparation of N-[10-Decarbamoyl-10-O-Thiocarbonylporfiromycin]Imidazole (Compound 6)

Using the preceding procedure and Compound 11 (Choi et al., *J. Org. Chem.*, 1995; Han et al., *J. Org. Chem.*, 1992) (14 mg, 0.05 mmol), 4-dimethylaminopyridine (2.8 mg, 0.02 mmol), and 1,1'-thiocarbonyldiimidazole (40.9 mg, 0.23 mmol) afforded Compound 6 (11.7 mg, 61%) as a purple solid: mp 89°–90° C.; HPLC t$_R$ (program 1) 35.1 min.;R$_f$ 0.51 (10% CH$_3$OH—CHCl$_3$); UV-vis (CH$_3$OH) 1$_{max}$ 360 nm; $^1$H NMR (CDCl$_3$) d 1.77 (s, C(6)CH$_3$), 2.17 (m, C(1)H, overlapped), 2.20 (s, N(1a)CH$_3$), 2.28–2.30 (m, C(2)H), 3.22 (s, C(9a)OCH$_3$), 3.49 (dd, J=1.6, 13.1 Hz, C(3)H$_a$), 3.82 (dd, J=4.9, 10.4 Hz, C(9)H), 4.24 (d, J=13.1

Hz, C(3)H$_b$), 4.91 (t, J=10.4 Hz, C(10)H H'), 5.18 (dd, J=4.9, 10.4 Hz, C(10)HH'), 5.24 (br, C(7)NH$_2$), 7.07 (s, imidazole C(4)H), 7.73 (s, imidazole C(5)H), 8.46 (s, imidazole C(2)H); $^{13}$C NMR (CDCl$_3$) 7.9, 42.4, 43.0, 43.3, 45.8, 49.8, 49.9, 70.7, 105.3, 105.8, 109.6, 117.9, 131.0, 136.9, 147.2, 155.0, 175.7, 178.4, 183.5 ppm; MS (+CI) m/e (rel intensity) 380 (6), 306 (6), 288 (M$^+$—OC(S)imidazole, 100); M$_r$ (+CI) 416.138 46 [M+1]$^+$ (calculated for C$_9$H$_{22}$N$_5$O$_4$S, 416.139 25).

EXAMPLE 5

Preparation of N-[10-Decarbamoyl-10-O-Carbonyl-(N(1a)-(Methylthio)Carbonyl)Mitomycin]Imidazole (Compound 7).

Utilizing the procedure for Compound 5 and anhydrous ethylene glycol dimethyl ether (2 μL) as the solvent, Compound 12 (14.8 mg, 0.04 mmol) and 4-dimethylaminopyridine (2.5 mg, 0.02 mmol) was treated with 1,1'-carbonyldiimidazole (33.0 mg, 0.20 mmol) to give Compound 7 (9.0 mg, 82%) as a purple solid: mp 94°–95° C.; HPLC t$_R$ (program 2) 29.8 min.; R$_f$ 0.42 (10% CH$_3$OH—CHCl$_3$); UV-vis (CH$_3$OH) 1$_{max}$ 360 nm; $^1$H NMR (CDCl$_3$) d 1.79 (s, C(6)CH$_3$), 2.31 (s, N(1a)C(O)SCH$_3$), 3.21 (s, C(9a)OCH$_3$), 3.37 (dd, J=1.5, 4.5 Hz, C(2)H), 3.48 (d, J=4.5 Hz, C(1)H), 3.57 (dd, J=1.5, 13.4 Hz, C(3)H$_a$), 3.82 (dd, J=5.4, 10.9 Hz, C(9)H), 4.48 (d, J=13.4 Hz, C(3)H$_b$), 4.56 (t, J=10.9 Hz, C(10)H H'), 5.15 (dd, J=5.4, 10.9 Hz, C(10)HH'), 5.15 (br, C(7)NH$_2$), 7.09 (s, imidazole C(4)H), 7.52 (s, imidazole C(5)H), 8.24 (s, imidazole C(2)H); $^{13}$C NMR (CDCl$_3$) 7.9, 12.9, 42.1, 42.2, 43.8, 48.9, 49.9, 64.8, 105.1, 105.4, 109.8, 117.3, 130.6, 137.3, 147.0, 148.2, 154.2, 175.9, 178.2, 179.6 ppm; MS (+CI) m/e (rel intensity) 460 [M+1, 100]$^+$, 366 (28), 348 (29), 154 (18); M$_r$ (+CI) 460.128 93 [M+1]$^+$ (calculated for C$_{20}$H$_{22}$N$_5$O$_6$S, 460.129 08).

EXAMPLE 6

Preparation of N-[10-Decarbamoyl-10-O-Thiocarbonyl-(N(1a)-(Methylthio)Carbonyl) Mitomvcinlimidazole (Compound 8).

Utilizing the procedure for Compound 5 and anhydrous ethylene glycol dimethyl ether (2 μL) as the solvent, Compound 12 (24.0 mg, 0.07 mmol) and 4-dimethylaminopyridine (4.0 mg, 0.03 mmol) was treated with 1,1'-thiocarbonyldiimidazole (58.5 mg, 0.33 mmol) to give Compound 8 (25 mg, 80%) as a purple solid: mp 92°–93° C.; HPLC t$_R$ (program 1) 38.2 min.; R$_f$ 0.56 (10% CH$_3$OH—CHCl$_3$); UV-vis (CH$_3$OH) 1$_{max}$ 360 nm; $^1$H NMR (CDCl$_3$) d 1.79 (s, C(6)CH$_3$), 2.26 (s, N(1a)C(O)SCH$_3$), 3.22 (s, C(9a)OCH$_3$), 3.37 (dd, J=1.5, 4.6 Hz, C(2)H), 3.47 (d, J=4.6 Hz, C(1)H), 3.56 (dd, J=1.5, 13.5 Hz, C(3)H$_a$), 3.93 (dd, J=4.8, 10.9 Hz, C(9)H), 4.48 (d, J=13.5 Hz, C(3)H$_b$), 4.78 (t, J=10.9 Hz, C(10)H H'), 5.49 (dd, J=4.8, 10.9 Hz, C(10)HH'), 5.23 (br, C(7)NH$_2$), 7.06 (s, imidazole C(4)H), 7.75 (s, imidazole C(5)H), 8.47 (s, imidazole C(2)H); $^{13}$C NMR (CDCl$_3$) 7.9, 13.0, 42.6, 42.2, 43.8, 48.9, 49.9, 69.4, 105.4, 105.5, 109.8, 118.1, 130.8, 137.0, 146.9, 154.4, 176.0, 178.2, 179.6, 183.4 ppm; MS (+CI) m/e (rel intensity) 348 (M+—OC(S)imidazole); M$_r$ (+CI) 476.105 64 [M+1]$^+$ (calculated for C$_{20}$H$_{22}$N$_5$O$_5$S$_2$, 476.106 24).

EXAMPLE 7

Preparation of 10-Des(Carbamoyloxy)-10-Azidoporfiromycin (Compound 14).

A dimethylformamide (1 μL) solution of Compound 13 (Kasai and Kono, *Syn. Lett.*, 1992; Choi et al., *J. Org. Chem.*, 1995; Urakawa et al., *J. Antibiot.*, 1981; Kono et al., *J. Antibiot.*, 1990) (6.6 mg, 0.017 mmol) and NaN$_3$ (9.1 mg, 0.14 mmol) was heated (about 90° C.) under Ar (1 hour), and then the solution was diluted with chloroform (about 10 μL), and filtered through a fritted funnel. The insoluble materials were washed with chloroform and partially concentrated in vacuo. The residue was purified by TLC (diethyl ether) to give Compound 14 as a dark brown solid (2.6 mg, 45%): HPLC t$_R$ 28.1 min. (program 1); R$_f$ 0.43 (ether); IR (KBr) 3437, 3329, 2100, 1601, 1555 cm$^{-1}$; UV-vis (CH$_3$OH) 1$_{max}$ 358 nm; $^1$H NMR (CDCl$_3$) d 1.27 (s, C(6)CH$_3$), 2.15 (overlapped dd, C(2)H), 2.27 (s, N(1a)CH$_3$), 2.42 (d, J=4.7 Hz, C(1)H), 3.17 (s, C(9a)OCH$_3$), 3.46 (dd, J=2.2, 12.9 Hz, C(3)H$_a$), 3.47 (m, C(9)H and C(10)HH'), 4.16 (d, J=11.5 Hz, C(10)HH'), 4.17 (d, J=12.9 Hz, C(3)H$_b$), 5.23 (br, C(7)NH$_2$); $^{13}$C NMR (CDCl$_3$) 7.9, 42.7, 43.3, 43.4, 46.0, 48.9, 49.7, 49.8, 105.2, 105.9, 110.7, 147.2, 154.5, 175.6, 178.5 ppm; MS (+CI) m/e (rel intensity) 331 [M+1, 93]$^+$, 330 [M, 100]$^+$; M$_r$ (+CI) 331.15096 [M+1]$^+$ (calculated for C$_{15}$H$_{19}$N$_6$O$_3$, 331.151 86), 330.143 11 |M|$^+$(calculated for C$_{15}$H$_{18}$N$_6$O$_3$, 330.144 04).

EXAMPLE 8

Preparation of 10-Des(Carbamoyloxy)-10-Aminoporfiromycin (Compound 15).

A pyridine solution (5 μL) containing Compound 14 (6.5 mg, 0.016 mmol) and a catalytic amount of PtO$_2$ was stirred under an atmosphere of H$_2$ at room temperature (2 h), and then 10 min. in the air. Methanol (2–3 drops) was added to the mixture and stirred (3 min.), and then the mixture was filtered through a Celite pad and the pad was washed with a minimum amount of warm methanol. The filtrate was concentrated in vacuo and the residue was purified by repetitive TLC (a: 10% methanol-chloroform, b: 20% methanol-chloroform) to obtain Compound 15 as a dark brown solid (3.3 mg, 55%): HPLC t$_R$ 10.6 min. (program 1); R$_f$ 0.24 (20% CH$_3$OH—CHCl$_3$); UV-vis (CH$_3$OH) 1$_{max}$ 362 nm; $^1$H NMR (pyridine-d$_5$) d 2.02 (s, C(6)CH$_3$), 2.15 (dd, J=2.1, 4.8 Hz, C(2)H), 2.15 (s, N(1a)CH$_3$), 2.59 (d, J=4.8 Hz, C(1)H), 3.16 (s, C(9a)OCH$_3$), 3.37 (t, J=5.8 Hz, C(9)H), 3.50 (dd, J=2.2, 12.9 Hz, C(3)H$_a$), 3.55 (m, C(10)HH'), 3.71 (dd, J=5.8, 12.3 Hz, C(10)HH'), 4.51 (d, J=12.9 Hz, C(3)H$_b$) (the C(7)NH$_2$ and C(10)NH$_2$ signals were not detected and are believed to be beneath the water peak); $^{13}$C NMR (pyridine-d$_5$) 8.8, 42.7, 42.9, 43.1, 46.0, 49.4, 50.7, 104.1, 107.9, 114.2, 155.5, 177.4, 178.6 ppm (two carbons were not detected); MS (+CI) m/e (rel intensity) 306 [M+1, 94]$^+$, 305 [M, 10]$^+$; M$_r$ (+CI) 305.160 82 [M+1]$^+$ (calculated for C$_{15}$H$_{20}$N$_4$O$_3$, 305.161 37).

EXAMPLE 9

Preparation of 10-Des(Carbamoyloxv)-10-Acetamidoporfiromycin (Compound 16).

Amine Compound 15 (1.0 mg, 3.40 mmol) was stirred in pyridine-d$_5$ (0.5 μL) under Ar in an ice-bath temperature, and then acetic anhydride (4 μL, 0.04 mmol) was injected and the ice bath removed. The reaction was stirred (30 min.), and then the reaction was concentrated by an Al stream and the residue was purified by TLC (5% CH$_3$OH—CHCl$_3$) to yield Compound 16 as a brown solid (0.9 mg, 79%): HPLC t$_R$ 21.1 min (program 1); R$_f$ 0.32 (5% CH$_3$OH-CHCl$_3$); $^1$H NMR (pyridine-d$_5$) d 2.02 (s, C(6)CH$_3$), 2.10 (s, COCH$_3$), 2.16 (dd, J=1.8, 4.8 Hz, C(2)H), 2.22 (s, N(1aCH$_3$), 2.48 (d, J=4.8 Hz, C(1)H), 3.10 (s, C(9a)OCH$_3$), 3.48 (dd, J=1.8, 12.9 Hz, C(3)H$_a$), 3.69 (t, J=7.5 Hz, C(9)H), 3.93 (ddd, J=2.1, 7.5, 13.1 Hz, C(10)HH'),4.43–4.53 (m, C(10)HH'), 4.56 (d, J=12.9 Hz, C(3)H$_b$), 8.56 (br t, J=2.1 Hz, NHCO) (the C(7)NH$_2$ was not detected and is believed to be beneath the water peak); $^{13}$C NMR (pyridine-d$_5$) 8.8, 23.4, 40.3, 42.9, 43.3, 44.0, 45.7, 49.5, 50.7, 104.3, 107.6, 113.8, 148.8, 156.0, 169.8, 177.6, 178.4 ppm; MS (+CI) m/e (rel intensity) 347 [M+1, 100]$^+$, 314 (M - 32, 60)$^+$; M$_r$ (+CI) 347, 172 13 [M+1]$^+$ (calculated for C$_{17}$H$_{23}$N$_4$O$_4$, 347.171 93).

EXAMPLE 10

Preparation of 10-Des(Carbamoyloxy)-10-Isothiocyanatoporfiromycin (Compound 9).

To a methylene chloride solution (2 μL) of di-2-pyridyl-thionocarbonate (4.6 mg, 0.02 mmol) was added dropwise a methylene chloride solution (0.5 μL) of Compound 15 (1.5 mg, 0.004 mmol) and then the reaction was stirred under Ar (2 hours). The volatile solvent was removed by a stream of Ar and the concentrated solution was purified by TLC (diethyl ether) to afford Compound 9 as a dark brown solid (1.4 mg, 84%): HPLC t$_R$=33.9 min. (program 1); R$_f$ 0.38 (25% hexane-ether); UV-vis (CH$_3$OH) 1$_{max}$ 362 nm; $^1$H NMR (pyridine-d$_5$) d 2.02 (s, C(6)CH$_3$), 2.21 (s, N(1a)CH$_3$), 2.24 (dd, J=2.1, 4.7 Hz, C(2)H), 2.57 (d, J=4.7 Hz, C(1)H), 3.16 (s, C(9a)OCH$_3$), 3.54 (dd, J=2.1, 12.9 Hz, C(3)H$_a$), 3.75 (dd, J=4.0, 11.1 Hz, C(9)H), 4.06 (dd, J=11.1, 14.3 Hz, C(10)HH'), 4.39 (d, J=12.9 Hz, C(3)H$_b$), 4.43 (dd, J=4.0, 14.3 Hz, C(10)HH') (the C(7)NH$_2$ was not detected and is believed to be beneath the water peak); $^{13}$C NMR (pyridine-d$_5$) 8.8, 42.9, 43.4, 43.5, 45.6, 45.9, 49.9, 50.5, 103.2, 106.3, 112.2, 128.7, 146.6, 155.3, 178.0, 181.2 ppm; MS (+CI) m/e (rel intensity) 347 [M+1, 100]$^+$, 346 [M, 53]$^+$, M$_r$ (+CI) 347.117 840 [M+1]$^+$ (calculated for C$_{16}$H$_{19}$N$_4$O$_3$S, 347.117 788).

EXAMPLE 11

Preparation of N-[10-Decarbamoyl-10-O-Carbonylporfiromycin]-Glycine Methyl Ester (Compound 18).

To a stirred methylene chloride solution (1 μL) of Compound 5 (1 mg, 0.003 mmol) and 4-dimethylaminopyridine (1.8 mg, 0.015 mmol) was added Compound 17 (1.6 mg, 0.01 mmol). The reaction mixture was stirred at room temperature (25 h), and then the solvent was removed under reduced pressure to give a crude purple solid. Purification by TLC (10% methanol-chloroform) afforded Compound 18 (0.6 mg, 57%) as a purple solid: mp 89°–90° C.; HPLC t$_R$ (program 2) 22.8 min.; R$_f$ 0.42 (10% CH$_3$OH—CHCl$_3$); UV-vis (CH$_3$OH) 1$_{max}$ 360 nm; $^1$H NMR (CDCl$_3$) d 1.75 (s, C(6)CH$_3$), 2.25 (s, N(1aCH$_3$), 2.25 (m, C(1)H, overlapped), 2.32–2.33 (m, C(2)H), 3.18 (s, C(9a)OCH$_3$), 3.44–3.50 (m, NHCH$_2$CO$_2$CH$_3$), 3.59 (dd, J=4.3, 10.8 Hz, C(9)H), 3.76 (s, CO$_2$CH$_3$), 3.99 (dd, J=6.0, 14.0 Hz, C(3)H$_a$), 4.20 (d, J=14.0 Hz, C(3)H$_b$), 4.41 (t, J=10.8 Hz, C(10)H H'), 4.71 (dd, J=4.3, 10.8 Hz, C(10)HH'), 5.20 (br, C(7)NH$_2$), 5.28 (br, NHCH$_2$CO$_2$CH$_3$); the assignment was further confirmed by the COSY spectrum; $^{13}$C NMR (CDCl$_3$) 7.9, 42.6, 42.8, 43.2, 46.0, 49.7 (2 C), 52.3, 62.7, 105.1, 105.6, 110.1, 147.3, 154.6, 156.0, 170.5, 175.6, 178.6 ppm; the remaining carbon signal was not detected; MS (+CI) m/e (rel intensity) 421 [M+1, 100]$^+$, 288 (8), 256 (15), 154 (5); M$_r$ (+CI) 421.173 29 [M+1]$^+$ (calculated for C$_{19}$H$_{25}$N$_4$O$_7$, 421.172 32).

An aqueous solution (0.5 μL) containing Compound 5 (3.0 mg, 0.0075 mmol) was adjusted to pH 9.0 with dimethylaminopyridine and then Compound 17 (4.7 mg, 0.038 mmol) was added. The reaction was stirred at room temperature and monitored by HPLC (program 2). After 19 hours no evidence of Compound 18 was observed and the major product was Compound 10.

EXAMPLE 12

Preparation of N-[10-Decarbamoyl-10-O-Thiocarbonylporfiromycin] Glycine Methyl Ester (Compound 19).

Utilizing the procedure for Compound 18 and using Compound 6 (9.5 mg, 0.02 mmol), 4-dimethylaminopyridine (16.8 mg, 0.14 mmol), and Compound 17 (14.4 mg, 0.11 mmol) afforded Compound 19 (8.4 mg, 84%): mp 83°–84° C.; HPLC t$_R$ (program 1) 29.6 min.; R$_f$ 0.43 (10% CH$_3$OH—CHCl$_3$); UV-vis (CH$_3$OH) 1$_{max}$ 360 nm; $^1$H NMR (CDCl$_3$) d 1.75 (s, C(6)CH$_3$), 2.25 (s, N(1a) CH$_3$), 3.19 (s, C(9a)OCH$_3$), 3.17 (dd, J=1.8, 4.8 Hz, C(2)H), 3.46 (d, J=4.8 Hz, C(1)H), 3.66–3.69 (m, NHCH$_2$CO$_2$CH$_3$), 3.71–3.73 (m, C(3)H$_a$, partially overlapped), 4.35 (dd, J=4.6, 10.7 Hz, C(9)H), 3.79 (s, CO$_2$CH$_3$), 4.71 (t, J=10.7 Hz, C(10)H H'), 4.20 (d, J=13.1 Hz, C(3)H$_b$), 4.96 (dd, J=4.6, 10.7 Hz, C(10)HH'), 5.23 (br, C(7)NH$_2$), 6.92 (br, NH CO$_2$CH$_3$); the assignment was further confirmed by the COSY spectrum; $^{13}$C NMR (CDCl$_3$) 7.9, 42.6, 42.7, 43.4, 46.0, 46.5, 49.7, 49.7, 52.5, 68.0, 105.0, 105.9, 109.9, 147.3, 154.7, 169.5, 175.6, 178.5, 190.3 ppm; MS (+CI) m/e (rel intensity) 306 (M$^+$—C(S)N(H)CH$_2$CO$_2$CH$_3$, 32), 288 (84), 256 (100); M$_r$ (+CI) 437.148 80 [M+1]$^+$ (calculated for C$_{19}$H$_{25}$N$_4$O$_6$S, 437.149 48).

EXAMPLE 13

Preparation of N-[10-Decarbamoyl-10-O-thiocarbonylporfiromycin] glycine Methyl Ester (Compound 19) Under Aqueous Conditions.

To a 20% methanolic-aqueous 0.05M borax buffer solution (pH 8.0, 0.5 μL) containing Compound 6 (1.6 mg, 0.004 mmol) was added Compound 17 (2.4 mg, 0.02 mmol). The reaction was stirred at 30° C. and monitored by HPLC (program 2). After 24 hours the ratio of Compound 19 to Compound 6 was 18:1. Formation of Compound 19 was confirmed by co-injection of an authentic sample of Compound 19 with the reaction mixture in the HPLC.

EXAMPLE 14

Preparation of N-[10-Decarbamoyl-10-O-carbonyl-(N(1a) -(methylthio)carbonyl)mitomycin] Methyl Ester (Compound 20).

Utilizing the procedure for Compound 18 and using Compound 7 (1.0 mg, 0.002 mmol), 4-dimethylaminopyridine (1.5 mg, 0.01 mmol) and Compound 17 (1.4 mg, 0.01 mmol) gave Compound 20 (0.5 mg, 48%): mp 102°–103° C. (d); HPLC t$_R$ (program 2) 27.4 min.; R$_f$ 0.33 (10% CH$_3$OH—CHCl$_3$); UV-vis (CH$_3$OH) 1$_{max}$ 360 nm; $^1$H NMR (CDCl$_3$) d 1.76 (s, C(6)CH$_3$), 2.29 (s, N(1a)C(O)SCH$_3$), 3.18 (s, C(9a)OCH$_3$), 3.33 (dd, J=1.7, 4.8 Hz, C(2)H), 3.49 (d, J=1.7 Hz, C(1)H), 3.54–3.57 (m, NHCH$_2$CO$_2$CH$_3$), 3.65–3.69 (m, C(3)H$_a$, partially overlapped), 3.71 (dd, J=4.6, 10.9 Hz, C(9)H), 3.76 (s, CO$_2$CH$_3$), 4.20 (t, J=10.9 Hz, C(10)H H'), 4.46 (d, J=13.5 Hz, C(3)H$_b$), 4.96 (dd, J=4.6, 10.9 Hz, C(10)HH'), 5.30 (br, C(7)NH$_2$), 5.41 (br, NH CO$_2$CH$_3$); $^{13}$C NMR (CDCl$_3$) 7.9, 13.0, 41.9, 42.0, 42.7, 44.2, 48.7, 49.7, 52.3, 62.2, 105.1, 105.5, 110.4, 147.1, 154.0, 170.5, 175.8, 178.4, 179.9, 181.6 ppm; MS (+CI) m/e (rel intensity) 481 [M+1, 6]⁺, 366 (10), 348 (35), 318(27), 316 (100), 270 (22), 116 (11); M, (+CI) 481.138 65 [M+1]⁺ (calculated for $C_{20}H_{25}N_4O_8S$, 481.139 31).

EXAMPLE 15

Preparation of N-|10-Decarbamoyl-10-O-Carbonyl-(N(1a) -(Methylthio)Carbonyl)Mitomycin]Glycine Methyl Ester (Compound 20) Under Aqueous Conditions.

Mitomycin Compound 7 (2.0 mg, 0.004 mmol) was added to a 20% methanolic-aqueous 0.05M borax buffer solution (pH 8.0, 0.5 µL) containing Compound 17 (2.7 mg, 0.02 mmol) and the resulting solution was stirred at room temperature (5 d). The progress of the reaction was monitored by HPLC (program 2). The HPLC analysis of the reaction mixture indicated the presence of five major peaks ($t_R$: 18.2, 25.1, 27.4, 29.6, 30.1 min.). Two of these corresponded to Compound 2 (18.2 min.) and Compound 7 (25.1 min.) and were identified by co-injection of authentic samples with the reaction mixture in the HPLC. The peaks at 27.4, 29.6, and 30.1 minutes have been tentatively assigned as Compounds 20, 17, and 11, respectively. The solvent was removed under reduced pressure to give a crude purple solid. Purification by preparative TLC (10% methanol-chloroform) afforded Compound 20 (0.7 mg, 36 %) as a purple solid: mp 102°–103° C. (d); HPLC $t_R$(program 2) 27.4 min.; $R_f$ 0.33 (10% $CH_3OH$—$CHCl_3$); ¹H NMR ($CDCl_3$) d 1.76 (s, C(6)$CH_3$), 2.30 (s, N(1a)C(O)$SCH_3$), 3.19 (s, C(9a)$OCH_3$), 3.33–3.40 (m, C(2)H), 3.51–3.52 (m, C(1)H), 3.55–3.56 (m, $NHCH_2CO_2CH_3$), 3.61–3.68 (m, C(3)$H_b$, partially overlapped), 3.70–3.75 (m, C(9)H), 3.77 (s, $CO_2CH_3$), 4.02–4.06 (m, C(10)H H'), 4.47 (d, J=13.5 Hz, C(3)$H_a$), 4.96–5.01 (m, C(10)HH'), 5.18–5.30 (br, C(7)$NH_2$), 5.32–5.39 (br, NH $CO_2CH_3$).

EXAMPLE 16

Preparation of N-|10-Decarbamoyl-10-O-thiocarbonyl-(N(1a) -(methylthio)carbonyl) mitomycin]Glycine Methyl Ester (Compound 21).

Utilizing the procedure for Compound 18, and using Compound 8 (14.0 mg, 0.03 mmol), 4-dimethylaminopyridine (21.6 mg, 0.18 mmol) and Compound 17 (18.5 mg, 0.15 mmol) gave Compound 21 (12.0 mg, 83%) [as a purple solid: mp 95°–96° C.; HPLC $t_R$(program 1) 35.2 min.; $R_f$ 0.51 (10% $CH_3OH$—$CHCl_3$); UV-vis (MeOH) $1_{max}$360 nm; ¹H NMR ($CDCl_3$) d 1.77 (s, C(6)$CH_3$), 2.30 (s, N(1a)C(O)$SCH_3$), 3.19 (s, C(9a)$OCH_3$), 3.33–3.35 (m, C(2)H), 3.48–3.49 (m, C(1)H), 3.51–3.57 (m, $NHCH_2CO_2CH_3$), 3.71–3.76 (m, C(3)$H_b$, partially overlapped), 3.83–3.85 (m, C(9)H), 3.80 (s, $CO_2CH_3$), 4.35–4.40 (m, C(10)H H'), 4.44–4.51 (m, C(3)$H_a$), 5.44 (dd, J=4.9, 10.96 Hz, C(10)HH'), 5.28–5.29 (br, C(7)$NH_2$), 6.98–7.01 (br, NH $CO_2CH_3$); the assignment was further confirmed by the COSY spectrum; ¹³C NMR ($CDCl_3$) 7.9, 13.0, 41.9, 42.2, 44.2, 46.6, 48.8, 49.8, 52.5, 67.0, 105.1, 105.5, 110.4, 147.1, 154.0, 169.5, 175.8, 178.4, 180.0, 190.1 ppm; MS (+CI) m/e (rel intensity) 497 [M+1,100]⁺, 348 (69), 316 (61), 182 (19); M, (+CI) 497.116 38 [M+1]⁺ (calculated for $C_{20}H_{25}N_4O_7S_2$, 497.116 46).

EXAMPLE 17

Preparation Of N-|10Decarbamoyl-10-O-Thiocarbonyl-(N(1a) -(Methylthio)Carbonyl) Mitomycin1]Glycine Methyl Ester (Compound 21) Under Aqueous Conditions.

To a 20% methanolic-aqueous 0.05M borax buffer solution (pH 8.0, 0.5 µL) containing Compound 8 (2.4 mg, 0.005 mmol) was added Compound 17 (3.2 mg, 0.03 mmol). The reaction was stiITed at 30° C. and monitored by HPLC (program 2). After 48 h, the complete consumption of Compound 8 was observed with only the production of Compound 21. Formation of Compound 21 was confirmed by co-injection of an authentic sample of Compound 21 with the reaction mixture in the HPLC.

EXAMPLE 18

Conjugation of the N-|10-Decarbamoyl-10-O-thiocarbonyl-(N(1a)-(methylthio)carbonyl) mitomycin]imidazole (Compound 8) to 5'-$H_2N$ $(CH_2)_6$-P(S) (OH)-GGCCCCGTGGTGGCTCCAT (SEQ ID NO:1) (Analytical Scale).

A stock solution (45 mM) of Compound 8 (2.6 mg, 5.4 mmol) in acetonitrile (120 µL) was prepared and then 10 µL (646 nmol) of this solution was added to an aqueous solution (50 µL) of SEQ ID NO: 1 (22.7 nmol). The final volume of the reaction was adjusted to 100 µL by the addition of an aqueous 0.2M Tris-HCl solution (pH 8.3). The reaction mixture was vortexed and stored at 5°–10° C. After 24 h, the ratio of Compound 23 to SEQ ID NO: 1 was 0.6:1 (260 nm), and the ratio of Compounds 8, 12, and 10 was 11:27:1 (365 nm) (HPLC analysis). The identities of Compounds 8, 12, and 10 were verified by co-injection of authentic samples with the reaction mixture in the HPLC.

EXAMPLE 19

Conjugation of the N-|10-Decarbamoyl-10-O-thiocarbonyl-(N(1a) -(methylthio)carbonyl) mitomycin]imidazole (Compound 8) to 5'-$H_2N$ $(CH_2)$-P(S) OH-GGCCCCGTGGTGGCTCCAT (Preparative Scale).

An acetonitrile stock solution (32 mM) of Compound 8 (60 µL, 2 mmol) was added to an aqueous Tris-HCl buffered solution (0.32 mM, 300 µL, pH 8.3) containing SEQ ID NO: 1 (96 nmol) and then the final volume was adjusted to 600 µL by the addition of an aqueous 0.2M Tris-HCl solution (pH 8.3). The reaction was kept undisturbed at room temperature (6 h). Purification of the reaction mixture was accomplished using semi-preparative HPLC (Rainin, flow rate 2.0 µL/min.). The solvent was evaporated in vacuo. The DNA/porfiromycin ratio was determined by UV-vis spectroscopy by measuring the relative absorbances at 260 and 360 nm, respectively. The e-values for purines, pyrimidines, and porfiromycin at 260 nm were considered to be 14.000, 7.000, and 12.000, respectively; and the e-values for porfiromycin and DNA at 360 nm were considered to be 23.000 and 0, respectively. 3 UV-vis analysis of the isolated product showed that the relative absorption at 260 nm:360 nm was 8:1 (calculated 8.7:1); HPLC $t_R$(program 1, Waters) 17.6 min.

EXAMPLE 20

Conjugation of 10Des(carbamoyloxy)-10-isothiocyanato-porfiromycin (Compound 9) to Oligodeoxynucleotides Compounds 32–35.

Oligodeoxynucleotides Compounds 32–35 supplied as the ammonium salts were converted to the corresponding sodium salts by dissolution in aqueous 0.1M NaOH and then the solution was lyophilized. The residue was re-dissolved in water and then neutralized with an aqueous 0.1M HCl solution and the final volume adjusted to 100 µL with water.

To an aqueous 0.2M NaHCO$_3$ buffer solution (10 μL, pH 9.0) was added an equal volume of the oligodeoxynucleotide stock solution (Compounds 32–35) and then a dimethylformamide solution (20 μL) of Compound 9 (860 nmol) was added. The solution was vortexed and then centrifuged (4000 rpm, 1 min.) and then allowed to stand at room temperature (24–30 h). The conjugated product was isolated using semi-preparative HPLC (Rainin, flow rate: 2.0 μL/min.). The fractions containing the conjugated product were collected and combined, and then the volatile solvents removed with a stream of N$_2$. The remaining solution was lyophilized and the light purple residue was re-dissolved in water (200 μL) and lyophilized to remove the remaining triethylammonium acetate. The products were analyzed by HPLC, UV-vis spectroscopy, and electrospray mass spectrometry.

EXAMPLE 21

Preparation of Compound 28.

Using Compound 32 (158 nmol) gave Compound 28 (158 nmol) in near quantitative yield: HPLC $t_R$(program 1) 21.6 min.; UV-vis 260 nm:360 nm =11.6:1 (calculated 10.9: 1), which corresponds to 1.06 equivalents of Compound 32 to 1 equivalent of Compound 9; MS (-ESI) 8511.1 [M+1]$^+$ (calculated for Compound 28, 8510.6) (MS (-ESI) of Compound 32: 8163.3 [M]$^+$ (calculated for Compound 32, 8163.2).

EXAMPLE 22

Preparation of Compound 29.

Using Compound 33 (158 nmol) gave Compound 29 (92 nmol, 58%): HPLC $t_R$(program 1) 21.9 min.; UV-vis 260 nm:360 nm=10.3:1 (calculated 10.5:1), which corresponds to 0.98 equivalents of Compound 33 to 1 equivalent of Compound 9; MS (-ESI) 8486.5 [M+1]$^+$ (calculated for Compound 29, 8486.6) (MS (-ESI) of Compound 33: 8139.4 [M+1]$^+$ (calculated for Compound 33, 8139.2).

EXAMPLE 23

Preparation of Compound 30.

Using Compound 34 (149 nmol) gave Compound 30 (111 nmol, 75%): HPLC $t_R$(program 1) 22.5 min.; UV-vis 260 nm:360 nm=11.0:1 (calculated 10.3:1), which corresponds to 1.07 equivalents of Compound 34 to 1 equivalent of Compound 9; MS (-ESI) 8446.2 [M+1]$^+$ (calculated for Compound 30, 8446.8) (MS (-ESI) of Compound 34: 8099.2 [M+1]$^+$ (calculated for Compound 34, 8099.2).

EXAMPLE 24

Preparation of Compound 31.

Using Compound 35 (170 nmol) gave Compound 31 (21 nmol, 12%): HPLC $t_R$(program 1) 23.8 min.; UV-vis 260 nm:360 nm=13.8:1 (calculated 10.3:1), which corresponds to 1.33 equivalents of Compound 35 to 1 equivalent of Compound 9; MS (-ESI) 8462.2 [M+2]$^+$ (calculated for Compound 31, 8461.5) (MS (-ESI) of Compound 35: 8113.9 [M]$^+$ (calculated for Compound 35, 8113.1).

---

What is claimed is:

1. A conjugate comprising an antisense oligonucleotide conjugated to the carbon atom at position 10 of mitomycin C or a derivative thereof.

2. The conjugate of claim 1 wherein the antisense oligonucleotide is conjugated to mitomycin C via an alkylamino spacer group attached to the 5' end of the oligonucleotide.

3. The conjugate of claim 2 wherein the spacer group contains one to 10 carbon atoms.

4. The conjugate of claim 3 wherein the alkylamino group contains five or six carbon atoms.

5. The conjugate of claim 1 wherein the oligonucleotide contains from about 10 to about 50 nucleotides.

6. The conjugate of claim 5 wherein the oligonucleotide contains from about 20 to about 40 nucleotides.

7. The conjugate of claim 1 wherein nucleotides of the oligonucleotide are linked by pseudophosphate bonds resistant to cleavage by exo- or endonucleases.

8. The conjugate of claim 3 having the structure I, below:

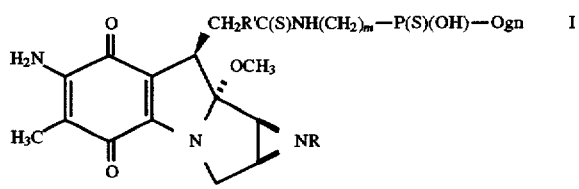

where R is H, $CH_3$ or $C(O)SCH_3$, R' is O or NH, m is an integer from 1 to 10 and Ogn is an antisense oligonucleotide.

9. The conjugate of claim 8 wherein R is $CH_3$, R' is NH and m is 5 or 6.

10. The conjugate of claim 8 wherein the Ogn has the nucleotide sequence of any of SEQ ID NOs: 1–6.

11. A pharmaceutical composition comprising a conjugate of claim 1 in a physiologically acceptable carrier.

12. A process of inhibiting expression of a gene in a vascular smooth muscle cell comprising exposing the cell to a conjugate of claim 1 containing an antisense oligonucleotide that hybridizes to a portion of the gene and inhibits expression of the gene.

13. The process of claim 12 wherein the gene is the human A-raf-1 gene and the oligonucleotide has the nucleotide sequence of SEQ ID NO: 1.

14. The process of claim 12 wherein the gene is the human fibroblast growth factor receptor 1 gene and the oligonucleotide has the nucleotide sequence of any of SEQ ID NOs: 2–6.

15. A process of inhibiting vascular smooth muscle cell proliferation comprising exposing the vascular smooth muscle cell to a conjugate of claim 1 wherein the Ogn is an antisense oligonucleotide directed against the human A-raf-1 or human fibroblast growth factor receptor 1 gene.

16. The process of claim 15 wherein the oligonucleotide has the nucleotide sequence of any of SEQ ID NOs: 1–6.

* * * * *

UNITED STATES PATENT AND TRADEMARK OFFICE
CERTIFICATE OF CORRECTION

PATENT NO.: 5,776,907
DATED: July 7, 1998
INVENTOR(S): Harold L. Kohn, Nam Huh, Timothy P. Kogan and Ajay A. Rege It is hereby certified that error appear(s) in the above-identified patent and that said Letters Patent is hereby corrected as shown below:

Column 1, line 59, please delete "an d it s" and insert --and its--
Column 1, line 66, please delete "alkylaion" and insert --alkylation--
Column 2, line 16, please delete "anti viral" and insert --antiviral--
Column 2, line 20, please delete "Chem." and insert --Coll.--
Column 2, line 41, please delete "oligonucleofide" and insert --oligonucleotide--
Column 11, line 34, please delete "34+2" and insert --346± 2--
Column 13, line 50, please delete "Mass." and insert --MA.--
Column 17, line 8, please delete "$C_9$" and insert --$C_{19}$--
Column 17, line 40, please delete "MitomvicinlImidazole and insert --Mitomycin]Imidazole--
Column 17, line 66, please delete "Choi ct al." and insert --Chio et al.--
Column 18, line 60, please delete " Al" and insert --Ar--
Column 19, line 34, please delete "$C_6$" and insert --$C_{16}$--
Column 21, line 44, please delete "las" and insert --as--
Column 22, line 2, please delete "tilTed" and insert --stirred--
Column 22, line 34, please delete "$(Ch_2)$-P(S) OH" and insert --$(CH_2)_6$-P(S)OH--

Signed and Sealed this

Twentieth Day of March, 2001

*Attest:*

NICHOLAS P. GODICI

*Attesting Officer*   *Acting Director of the United States Patent and Trademark Office*